United States Patent
Shi et al.

(10) Patent No.: US 12,048,620 B2
(45) Date of Patent: Jul. 30, 2024

(54) FLEXIBLE INTESTINAL ANASTOMOSIS STENT

(71) Applicant: WENZHOU INSTITUTE, UNIVERSITY OF CHINESE ACADEMY OF SCIENCES, Wenzhou (CN)

(72) Inventors: Changcan Shi, Wenzhou (CN); Xujian Li, Wenzhou (CN); Zhixiao Ji, Wenzhou (CN); Luqi Pan, Wenzhou (CN); Xiao Yang, Wenzhou (CN)

(73) Assignee: WENZHOU INSTITUTE, UNIVERSITY OF CHINESE ACADEMY OF SCIENCES, Wenzhou (CN)

( * ) Notice: Subject to any disclaimer, the term of this patent is extended or adjusted under 35 U.S.C. 154(b) by 0 days.

(21) Appl. No.: 18/552,423

(22) PCT Filed: Apr. 25, 2022

(86) PCT No.: PCT/CN2022/088876
§ 371 (c)(1),
(2) Date: Sep. 25, 2023

(87) PCT Pub. No.: WO2023/060870
PCT Pub. Date: Apr. 20, 2023

(65) Prior Publication Data
US 2024/0099824 A1    Mar. 28, 2024

(30) Foreign Application Priority Data

Oct. 12, 2021 (CN) .......................... 202111190317.2

(51) Int. Cl.
*A61F 2/04* (2013.01)
*A61L 31/04* (2006.01)

(52) U.S. Cl.
CPC .............. *A61F 2/04* (2013.01); *A61L 31/041* (2013.01); *A61F 2002/045* (2013.01); *A61F 2240/001* (2013.01); *A61F 2250/0036* (2013.01)

(58) Field of Classification Search
CPC ................... A61F 2/04; A61F 2002/045; A61F 2240/001; A61F 2250/0036; A61L 31/041
See application file for complete search history.

(56) References Cited

U.S. PATENT DOCUMENTS

| | | |
|---|---|---|
| 2020/0029968 A1 | 1/2020 | Cai et al. |
| 2021/0113323 A1* | 4/2021 | Hedberg ................. A61F 2/064 |
| 2021/0236131 A1 | 8/2021 | Anderson et al. |

FOREIGN PATENT DOCUMENTS

| | | |
|---|---|---|
| CN | 101422382 A | 5/2009 |
| CN | 103239265 A | 8/2013 |
| (Continued) | | |

OTHER PUBLICATIONS

CN207445074U Translation (Year: 2018).*

*Primary Examiner* — Brian A Dukert
*Assistant Examiner* — Rebecca Lynee Zimmerman
(74) *Attorney, Agent, or Firm* — Christensen, Fonder, Dardi & Herbert PLLC

(57) ABSTRACT

A flexible intestinal anastomosis stent which sucks secretions on an inner wall of an intestinal tract and at a suture site into a horn-shaped channel through a through-hole. The secretion is discharged to an inside of the stent body through a liquid-inlet hole after being squeezed by intestinal tract contents, thereby reducing a risk of infection at the suture site. A lower edge of the outlet end of the stent body has a concave polygonal structure, each reflex angle at a lower edge of the concave polygonal structure being formed with one inwardly folded wrinkle structure on a side wall of the stent body, and the wrinkle structure also able to accommo- (Continued)

date the secretions. The lower edge is stressed and deformed by the intestinal tract contents to reduce a reflex angle, so that secretions in the wrinkle structure are discharged downwardly, such that risk of complications is reduced.

9 Claims, 3 Drawing Sheets

(56) References Cited

FOREIGN PATENT DOCUMENTS

| | | | |
|---|---|---|---|
| CN | 207445074 U | * | 6/2018 |
| CN | 207445074 U | | 6/2018 |
| CN | 109124714 A | | 1/2019 |
| CN | 109480943 A | | 3/2019 |
| CN | 110522485 A | | 12/2019 |
| CN | 210873625 U | | 6/2020 |
| CN | 111449707 A | | 7/2020 |
| CN | 113288505 A | | 8/2021 |
| CN | 113413491 A | | 9/2021 |
| CN | 113893390 A | | 1/2022 |

* cited by examiner

FLEXIBLE INTESTINAL ANASTOMOSIS STENT

RELATED APPLICATIONS

The present application is a National Phase entry of PCT Application No. PCT/CN2022/088876, filed Apr. 25, 2022, which claims priority to Chinese Patent Application No. 202111190317.2, filed Oct. 12, 2021, the disclosures of which are hereby incorporated by reference herein in their entirety.

TECHNICAL FIELD

The present disclosure relates to the technical field of gastrointestinal reconstruction anastomosis instruments and in particular to a novel flexible intestinal anastomosis stent.

BACKGROUND OF THE INVENTION

Gastrointestinal reconstruction anastomosis is one of the most common surgical procedures in abdominal surgery. In the past century of the development of gastrointestinal surgery, the incidence of anastomotic fistula has not decreased significantly, which has become one of the worldwide challenges to the success rate of gastrointestinal surgery. Intestinal lesions such as gastrointestinal benign and malignant tumors, gastrointestinal perforation, gastrointestinal obstruction, hemorrhage and ischemia, often require resection of part of the diseased intestinal tract before anastomosis. Traditional methods mostly use manual suture anastomosis. In recent decades, most use tubular stapler for end-to-end or end-to-side anastomosis, or linear cutter stapler for side-to-side anastomosis. Regardless of the anastomosis procedure, anastomotic fistula, a deadly complication, cannot be prevented.

At present, it is generally accepted and practiced by colorectal surgeons at home and abroad that temporary bypass surgery, such as temporary ileostomy or colostomy and other additional surgeons, can definitely avoid the complications caused by anastomotic fistula, but there is no literature to support whether it can reduce the occurrence probability of anastomotic fistula. However, the bypass surgery requires planned reoperation for reversion, and re-reversion also means re-gastrointestinal reconstruction and anastomosis. There is also the occurrence probability of anastomotic fistula, anastomotic stenosis and other related complications, but the occurrence probability is lower than that of the first operation. Achieving isolation of intestinal contents, especially fecal contents, in the area of the anastomotic stoma with good blood supply at both ends of the anastomotic stoma and without tension in apposition, and achieving relative isolation and a clean local environment is an effective strategy to prevent anastomotic fistula and complications such as peritonitis and abdominal abscess. The key technical bottleneck of realizing the strategy is the breakthrough of ideal auxiliary anastomosis material. The purpose of intestinal anastomosis is to restore the physical, histological and physiological function of the intestine at both ends of the anastomotic stoma. At present, the main problems of the conventional stapler include that: (1) metal staplers are not biodegradable, resulting in permanent retention in the body; (2) degradable high molecular material staplers lack mechanical matching with wound tissue; (3) the staplers lack the regulation and control function of tissue repair, and cannot reasonably regulate and control the recovery of normal intestinal function.

Clinically, all bowel anastomoses are performed consisting of the following steps: good preoperative preparation, appropriate surgical timing, scientific anastomosis (surgery) and meticulous postoperative management. Among them, the scientific anastomosis is the core, because it is directly related to the success or failure of surgery[9]. In theory, scientific anastomosis should have the following characteristics that: (1) the anastomosis effect is reliable, and the intestinal healing process after anastomosis conforms to its damage repair process under physiological conditions, with neither insufficient healing (anastomotic fistula) nor excessive healing (scar fibrosis, anastomotic stenosis); (2) the operation itself has little damage to the intestinal wall tissues at both ends of anastomotic stoma, and the foreign body reaction of the body caused by the early attachments of anastomotic stoma (sutures, metal staples, etc.) required for the operation is slight and disappears by itself after the completion of healing (ex vivo or in vivo degradation); (3) it is easy to operate, has strong generalization, and has a short learning curve; (4) the operation has strong versatility and can be used in a variety of surgical conditions, such as different surgical sites (small intestine, colorectal, etc.), different anastomosis methods (end-to-end, end-to-side, etc.) and different surgical opportunities (emergency or elective surgery), and even in complicated systemic or local abdominal conditions such as abdominal infection, chemotherapy status, malnutrition, etc.

Many domestic and foreign research centers have conducted various types of gastrointestinal tract "endoluminal stent" anastomosis research, in which the supporting carriers are mainly a variety of synthetic new polymer biodegradable materials, such as Detweiler MB, etc., which use a sliding absorbable intraluminal nontoxic stent (SAINT) to complete intestinal anastomosis. Buch N etc. uses a rapidly degrading (<2 h) polymeric stent prosthesis (Polyglycols@Hoechst SBStube) on the basis of conventional single-layer surgical colonic anastomosis, which could improve the mucosal epithelial covering of anastomotic stoma and the partial pressure of tissue oxygen. Tsereteli Z etc. uses the Polyflex™ stent made of polyester material in the animal model of postoperative anastomotic fistula after colon surgery, demonstrating that the Polynex™ stent can reduce postoperative complications and promote the healing of anastomotic fistula. The Netherlandish company Polyganics BV invented "C-Seal™", also a biodegradable polymer material, combined with stapler operation, which can reduce the incidence of anastomotic fistula in low colorectal surgery.

"Endoluminal stenting" is not only successful in the field of surgical intestinal anastomosis, but also excellent in digestive endoscopy. Self-expanding metallic stent (SEMS) is the representative of the most common endoscopic "endoluminal stenting". Not only can people use the endoluminal stenting for the treatment of gastrointestinal stenosis (or obstruction) diseases, but SEMS has been repeatedly proved to be applicable to the treatment of gastrointestinal perforation and anastomotic fistula, which originally require surgical treatment, although it is currently limited to selected cases. In 2009, AmraniL etc. introduced the concept of "stent-guided regeneration and re-epithelialization" and stated that the stent can divert and isolate the contents of digestive tract, so that the site to be healed (anastomosis or injury site) can be healed in an "undisturbed" environment, and that the stent can provide a platform for epithelial cells to crawl during the healing process, promoting "re-epithelialization". In recent years, the concept of "endoluminal vacuum therapy" (EVT) has been proposed in endoscopy, which is similar to that of endoluminal stent, i.e. the use of a "sponge-like" endoluminal implant, externally connected to negative pressure drainage, to direct the intestinal contents around the site to be healed, allowing the anastomosic stoma to heal under low pressure and relatively dry conditions.

Domestic patents related to intestinal repair devices are as follows: patent CN 111449707A proposes an anorectal stapler, including a handle base, a transmission assembly, a percussion assembly and a anastomosis-cutting assembly; the transmission assembly includes a screw rod arranged inside a handle seat and an adjustment mechanism arranged at a tail end of the handle seat and connected a the tail end of the screw rod; a nailing seat is fixedly mounted on a front end of the lead screw; the percussion assembly includes a movable handle provided on the handle seat and a straight push rod sheathed on the lead screw; the anastomosis-cutting assembly includes a staple pusher, a cartridge housing, a cartridge, and a circular knife. In this disclosure, the staple pusher, the staple cartridge sleeve and the staple cartridge are made of metal materials, and the components cannot be degraded in vivo, and can only be permanently retained in vivo or removed by secondary surgery. Patent CN109480943 A is made of degradable materials, adopts the method of nail body perforation and fixation, and designs a support frame at a rear end of the nail body. However, the anastomotic ring has large hardness and inelasticity, and cannot well adapt to intestinal peristalsis, with obvious foreign body sensation. Similarly, there is an invention patent CN103239265 A, in which the degradable materials polyglycolide and polylactide are used as raw materials for gastrointestinal anastomosis. The stapler has the function of fragile disassembly, but also lacks the mechanical matching with intestinal tissue. An ideal stapler should have the following characteristics: (1) effective isolation of intestinal contents; (2) the operation of stapler implantation having little damage to the intestinal wall of anastomosic stoma; (3) being easy to operate. The stapling devices currently on the market do not meet the above-mentioned requirements at the same time.

Based on all the foregoing application problems in endoscopic and surgical practice, we can conclude that: endoluminal isolation and endoluminal decompression promote bowel healing such that ideal healing can be safely achieved in high risk situations such as gastrointestinal perforation, anastomotic fistula, etc. In fact, the surgeon should be familiar with this conclusion, e.g. common gastrointestinal decompression and gastrostomy bypass in clinical work is the application of "intracavitary isolation and intracavitary decompression". "Intracavitary support method" is similar to using some polymer materials to transform traditional gastrointestinal "decompression+external drainage" into "support+internal drainage", which greatly improves the quality of life of patients. Furthermore, the implant can degrade itself after completing its function and does not remain in the body.

SUMMARY OF THE INVENTION

In order to solve the technical drawbacks of the prior art, the present disclosure provides a novel flexible intestinal anastomosis stent.

The technical solution adopted by the present disclosure is a novel flexible intestinal anastomosis stent, including a tubular stent body, which includes a side wall, wherein an upper end and a lower end of the stent body are respectively an inlet end and an outlet end, the side wall of the stent body being provided with a plurality of special-shaped through holes, the through holes being horn-shaped, a large opening of the horn-shaped through holes being a liquid inlet hole on an outer side of the stent body, and a small opening thereof being a liquid outlet hole on an inner side of the stent body, the liquid inlet hole of each of the through holes being close to a side of the inlet end of the stent body, and the liquid outlet hole being close to a side of the outlet end of the stent body, the stent body being made of a flexible material, and the horn-shaped through holes on the side wall being pressed and deformed to discharge secretion in the through holes to an inside of the stent body via the liquid inlet holes.

An annular upper edge of the inlet end is provided with a boss, a lower edge of the outlet end having a concave polygonal structure, each reflex angle of a lower edge of the concave polygonal structure being formed with one inwardly folded wrinkle structure on the side wall of the stent body, and the lower edge of the concave polygonal structure being stressed and deformed to make an angle degree of the reflex angle smaller.

The stent body includes a suture site, the suture site including the annular upper edge of the inlet end and inferior-angled edge 5 of the lower edge of the concave polygonal structure of the outlet end.

A length of the wrinkle structure is ½-⅔ of a height of the stent body.

A thickness of the inner wall of the stent body is 0.20-0.6 mm.

A thickness of the side wall, at the wrinkle structure, of the intestinal anastomosis stent is smaller than a thickness of the side wall above the wrinkle structure.

A depth of the horn-shaped through hole is greater than that of the side wall of the intestinal anastomosis stent.

A depth of the horn-shaped through hole is 1-2 mm

The stent body is made of a bio-flexible elastomer based on PTMC-b-PEG-b-PTMC copolymer blended with at least one of PLA, PCL and PBS, a content of PEG in the PTMC-b-PEG-b-PTMC copolymer is 10%-20%, and a blending ratio of the at least one of PLA, PCL and PBS is 5-30%.

The flexible intestinal anastomosis stent is prepared by the following steps:

(1) synthesis of PTMC-b-PEG-b-PTMC copolymer: the synthetic process needing to be operated in an anhydrous and oxygen-free environment, adding a solution of 95-80 wt % of TMC monomer, 5-20 wt % of PEG5000 and 1-5 wt % of catalyst $Sn(Oct)_2$ into a reaction tube, placing a magneton in the reaction tube, sealing a tube opening after ensuring that the reaction tube is anhydrous and oxygen-free, sealing the tube opening with a sealing film to ensure that no oxygen and moisture enter, placing the reaction tube into an oil bath for a reaction, a temperature being 120-150° C., a reaction time being 24-48 h, and after the reaction is finished, taking out the solution for use;

(2) dissolution of PTMC-b-PEG-b-PTMC: according to a solid-liquid ratio of 1:5, using $CHCl_3$ or DMF or THF to dissolve the PTMC-b-PEG-b-PTMC copolymer, first washing the inner wall with $CHCl_3$ or DMF or THF for a plurality of times, washing away silicone grease and unreacted monomers, then adding an excess of $CHCl_3$ or DMF or THF, placing the solution on a shaker, a temperature of the shaker being set at 37° C., and waiting for the solution to completely dissolve;

(3) purification of PTMC-b-PEG-b-PTMC: the dissolved solution being slowly poured into a beaker containing n-hexane or ethanol for purification, slowly poured and continuously stirred, and the obtained flocculent PTMC-b-PEG-b-PTMC being suction-filtered, followed by drying in a vacuum drying oven for 48 h;
(4) preparation of electrospinning solution: compounding a PTMC-b-PEG-b-PTMC copolymer and at least one of PLA, PCL, PBS into a solvent DMF/THF, DMF:THF=1:1, a mass fraction of the solution being 5-10 wt %, and the solution being placed on a constant temperature shaker at 37° C. for 24 h until complete dissolution, and the electrospinning operation being performed after the dissolution is complete;
(5) preparation of anastomosis tube by electrospinning: performing electrospinning on an electrospinning apparatus to obtain the flexible intestinal anastomosis stent, electrospinning parameters being: a voltage of (−5, 30) V; a needle pushing speed of V=1.0-5.0 ml/h; a roller speed of V=100-500 RPM; a temperature of T=25-35° C.; a humidity of WET=20-40%.

Advantageous effects of the present disclosure are that the present disclosure provides a novel flexible intestinal anastomosis stent, which has a three-dimensional reticulated micro-nano structure matching the elasticity of the intestinal tract, which sucks secretions on an inner wall of an intestinal tract and at a suture site into a horn-shaped channel through a horn-shaped through-hole provided, while since a liquid inlet hole of each through-hole is close to a side of an inlet end of a stent body and a liquid outlet hole is close to a side of an outlet end, the secretion in the channel is discharged to an inside of the stent body through the liquid inlet hole after being squeezed by intestinal contents, thereby reducing a risk of infection at the suture site of the inner wall of the intestinal tract, a lower edge of the outlet end of the stent body having a concave polygonal structure, each reflex angle at a lower edge of the concave polygonal structure being formed with one inwardly folded wrinkle structure on a side wall of the stent body, and the wrinkle structure also being able to accommodate the secretions on the inner wall of the intestinal tract and at the suture site, the lower edge of the concave polygonal structure being stressed and deformed by the intestinal contents to make an angle degree of the reflex angle smaller, so that secretions in the wrinkle structure are discharged downward in a wrinkle direction, and a probability of intestinal anastomotic fistula and other complications is significantly reduced.

Figure 1:
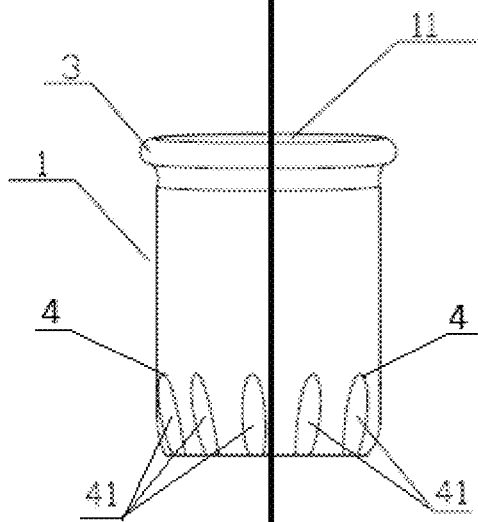
FIG. 1 is a schematic structural diagram of the present disclosure.
Figure 2:
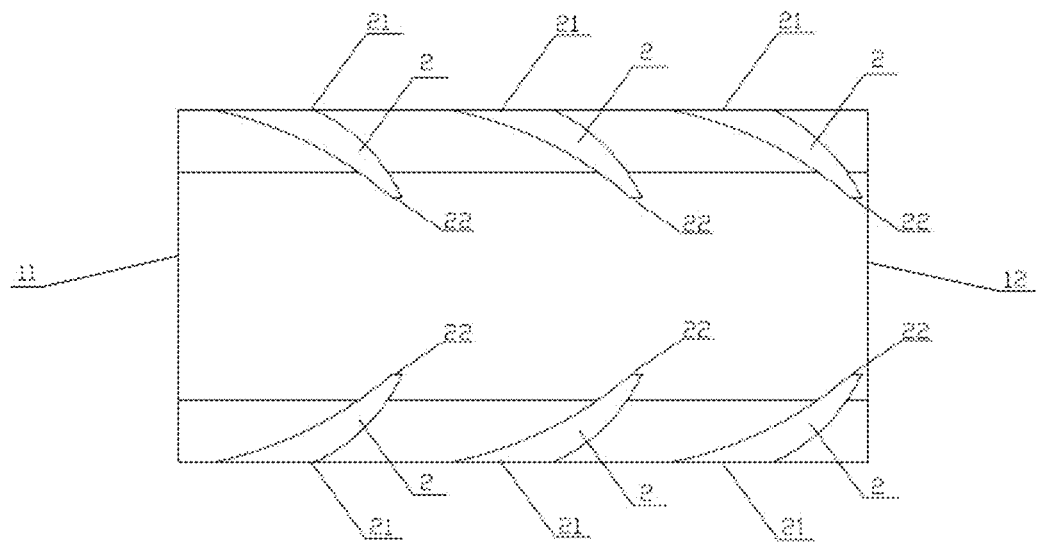
FIG. 2 is a cross-sectional structural diagram of a horn-shaped through hole of the present disclosure.
Figure 3:
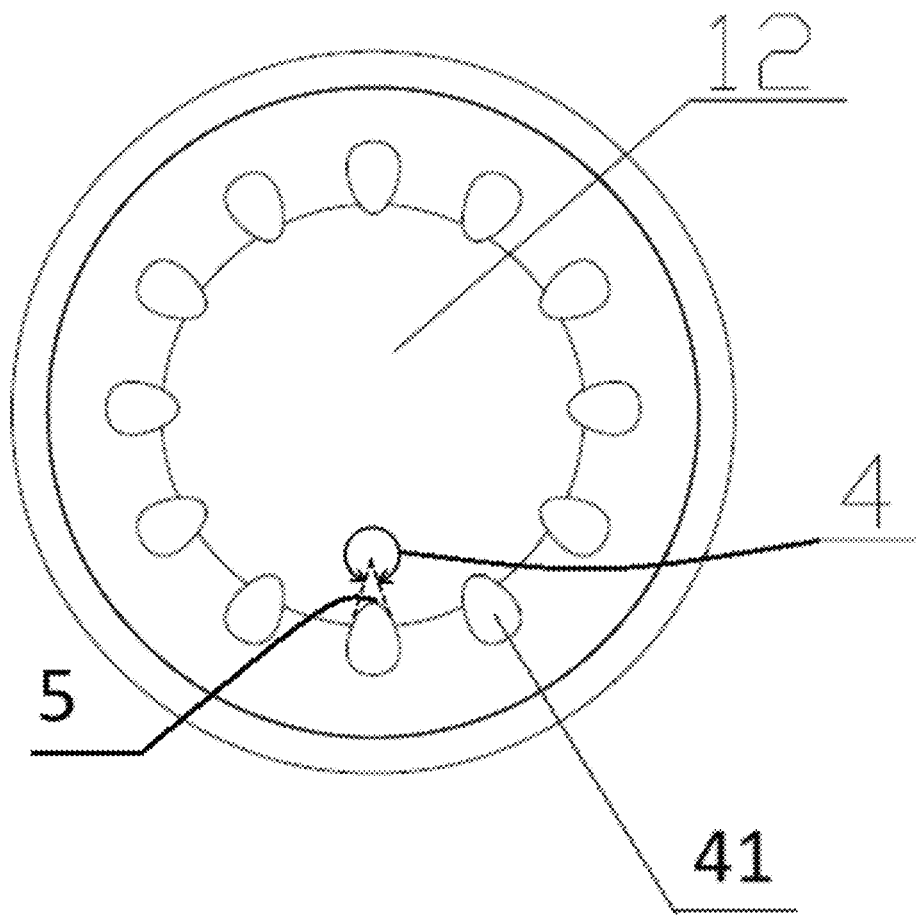
FIG. 3 is a schematic structural diagram of a lower edge of an outlet end of a stent body of the present disclosure.

In the drawings: 1—stent body, 2—through hole, 3—boss, 4—reflex angle, 11—inlet end, 12—outlet end, 21—liquid inlet hole, 22—liquid outlet hole, 41—wrinkle structure.

DETAILED DESCRIPTION OF THE INVENTION

The embodiments of the present disclosure will now be described more clearly and fully hereinafter with reference to the accompanying drawings, in which embodiments of the disclosure are shown. It is to be understood that the embodiments described are only a few, but not all embodiments of the disclosure. Based on the embodiments of the present disclosure, all other embodiments obtained by a person of ordinary skill in the art without inventive effort fall within the scope of the present disclosure.

Material Composition:

A bio-flexible elastomeric intestinal anastomosis stent based on a blend of PTMC-b-PEG-b-PTMC copolymer and at least one of PLA, PCL, PBS. The intestinal anastomosis stent is integrally made of PTMC-b-PEG-b-PTMC copolymer material and blended by compounding at least one of PLA, PCL and PBS. The PTMC-b-PEG-b-PTMC copolymer is a triblock PTMC-b-PEG-b-PTMC copolymer synthesized by ring-opening polymerization of high molecular medical materials TMC and PEG, the content of PEG in the PTMC-b-PEG-b-PTMC copolymer is 10%-20%, a blending ratio of at least one of the PLA, PCL and PBS is 5-30%, and a thickness of the intestinal anastomosis stent is 0.2-0.6 mm.

Manufacturing Process:

Electrospinning: preparation of electrospinning solution: a mass fraction of the solution is 5-10%, and a solvent is DMF/THF=1/1 (V/V). The PTMC-b-PEG-b-PTMC copolymer and at least one of PLA, PCL and PBS are compounded, added to the solvent and placed on a constant temperature shaker at 37° C. for 24 h until completely dissolved. The dissolved electrospinning solution is electrospun. Electrospinning conditions: a voltage of (−5, 30) V; a needle pushing speed of V=1.0-5.0 ml/h; a roller speed of V=100-500 RPM; a temperature of T=5-35° C.; a humidity of WET=20-40%.

The particular preparation method is as follows:
1. Synthesis of PTMC-b-PEG-b-PTMC copolymer: the synthetic process needing to be operated in an anhydrous and oxygen-free environment, adding a solution of 95-80 wt % of TMC monomer, 5-20 wt % of PEG5000 and 1-5 wt % of catalyst $Sn(Oct)_2$ into a reaction tube, placing a magneton in the reaction tube, sealing a tube opening with silicone grease after ensuring that the reaction tube is anhydrous and oxygen-free, sealing the tube opening with a sealing film to ensure that no oxygen and moisture enter; placing the reaction tube into an oil bath for a reaction, a temperature being 120-150° C., a reaction time being 24-48 h, and after the reaction is finished, taking out the solution for use.
2. Dissolution of PTMC-b-PEG-b-PTMC: according to a solid-liquid ratio of 1:5, using $CHCl_3$ or DMF or THF to dissolve the synthesized material; first washing the inner wall with $CHCl_3$ or DMF or THF for a plurality of times, washing away silicone grease and unreacted monomers, then adding an excess of $CHCl_3$ or DMF or THF, placing the solution on a shaker, a temperature of the shaker being set at 37° C., and waiting for the solution to completely dissolve.
3. Purification of PTMC-b-PEG-b-PTMC: the dissolved solution being slowly poured into a beaker containing n-hexane or ethanol for purification, slowly poured and continuously stirred with a glass rod; the obtained flocculent PTMC-b-PEG-b-PTMC being suction-filtered, followed by drying in a vacuum drying oven for 48 h.
4. Preparation of electrospinning solution: the substances used are dissolved in the solvent DMF/THF (DMF:THF=1:1), and the mass fraction of the solution is 5-10 wt %. The PTMC-b-PEG-b-PTMC copolymer and at least one of PLA, PCL and PBS are compounded, added to the solvent DMF/THF (DMF:THF=1:1) and placed on a constant temperature shaker at 37° C. for 24 h until completely dissolved. After dissolution is complete, the electrospinning operation is performed.

5. Preparation of anastomosis tube by electrospinning: spinning being performed on an electrospinning model TL-Pro-BM. The parameter settings are as follows: a voltage of (−5, 30) V; a needle pushing speed of V=1.0-5.0 ml/h; a roller speed of V=100-500 RPM; a temperature of T=5-35° C.; a humidity of WET=20-40%.

TABLE 1

Electrospinning conditions

| Needle pushing speed (mL/h) | Distance from needle to receiver (cm) | Roller speed ~~(RMP)~~ (RPM) | Voltage range (V) | Temperature (° C.) | Humidity (%) |
|---|---|---|---|---|---|
| 0.9 | 20 | 400 | −1, 20 | 35 | 25 |

Figure 4:
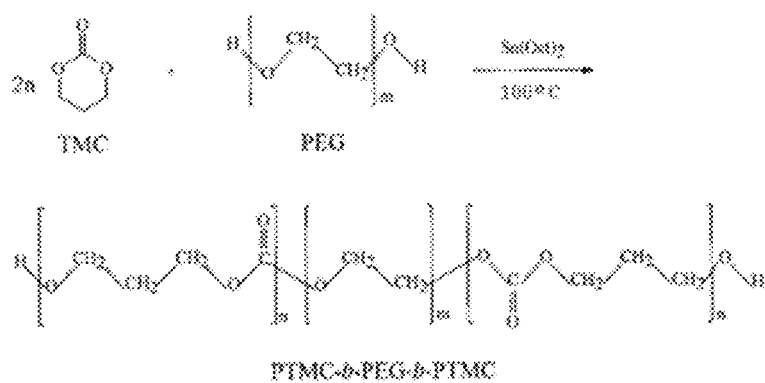
FIG. 4 is a reaction mechanism diagram of a PTMC-b-PEG-b-PTMC triblock copolymer of the present disclosure.
Figure 5:
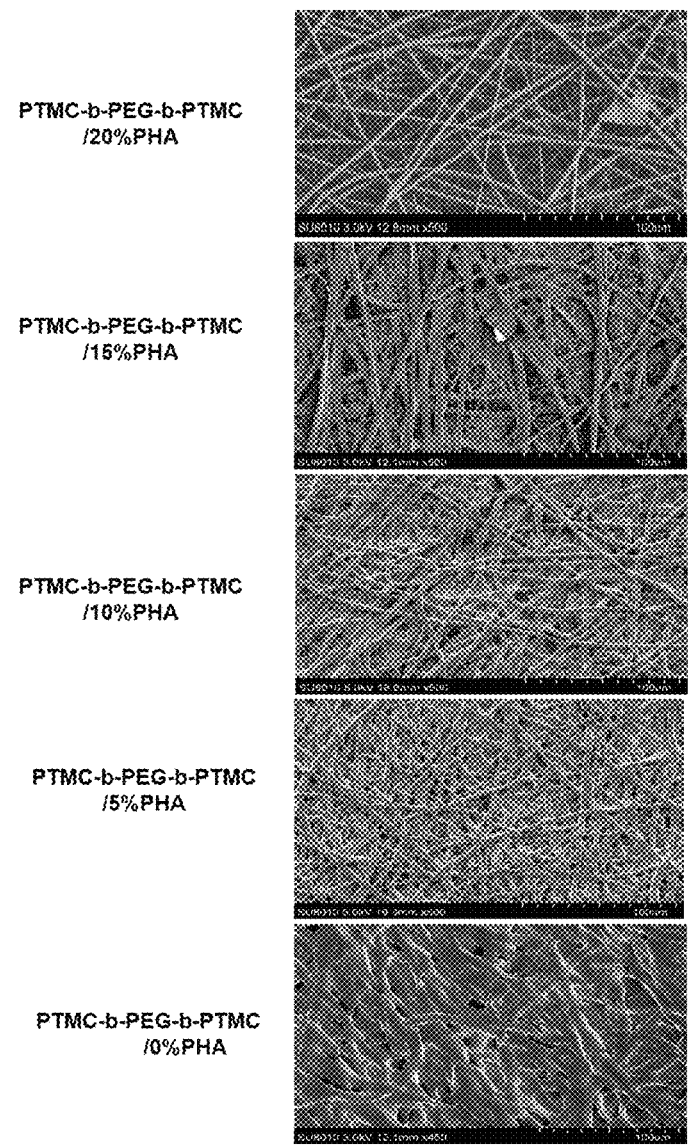
FIG. 5 is a SEM photograph of PTMC-b-PEG-b-PTMC copolymer electrospinning stent of the present disclosure with different PEG contents.

PTMC-b-PEG-b-PTMC triblock copolymers are synthesized by ring-opening polymerization of trimethylene carbonate initiated by polyethylene glycol hydroxyl groups (FIG. 4). Under the catalysis of $Sn(Oct)_2$, TMC is copolymerized with PEG to form PTMC-b-PEG-b-PTMC block copolymer. The copolymerization with different PEG block ratios and the physical properties of the product fractions are shown in Table 2.

TABLE 2

Composition and physical properties of PTMC-b-PEG-b-PTMC copolymer

| Sample ID | Sample name | PEG wt % | $Mn(10^3)$ | $[\eta]$ (dL/g) |
|---|---|---|---|---|
| PTMC-PEG-PTMC$_1$ | PEG20% | 20 | 25.85 | 0.586 |
| PTMC-PEG-PTMC$_2$ | PEG15% | 15 | 34.66 | 0.770 |
| PTMC-PEG-PTMC$_3$ | PEG10% | 10 | 51.93 | 0.927 |
| PTMC-PEG-PTMC$_4$ | PEG5% | 5 | 72.38 | 1.288 |

The degradation rate and mechanical properties of block copolymers with different molecular weights are very different. Different feed ratios have a significant impact on the molecular weight of block copolymers. Implantation in the intestinal tract requires the products to have a suitable degradation rate and excellent mechanical properties. Therefore, this experiment focuses on the impact of different ratios of TMC monomer and PEG in the raw materials on the molecular weight and properties of block copolymer PTMC-b-PEG-b-PTMC. The factors of different mass ratios of TMC monomer to PEG in raw materials are studied, and the reaction time is controlled at 24 h. The results are shown in Table 2. The data show that as the proportion of PEG in the raw materials decreases, the intrinsic viscosity of PTMC-b-PEG-b-PTMC increases and the molecular weight increases.

TABLE 3

Hydrophobicity and mechanical properties of PTMC-b-PEG-b-PTMC copolymer with different PEG content

| Sample name | PEG20% | PEG15% | PEG10% | PEG5% | PEG0% |
|---|---|---|---|---|---|
| Contact angle (°) | 45.6 | 55.8 | 63.4 | 72.2 | 85.6 |
| Tensile strength (MPa) | 6.38 | 8.62 | 10.26 | 12.75 | 14.42 |

The good hydrophilicity of the material makes it more biocompatible, so in order to evaluate the hydrophilicity and hydrophobicity of PTMC-b-PEG-b-PTMC, a water contact angle of the sample surface is measured by dynamic contact angle experiment and is listed in Table 3. The results clearly show that the dynamic contact angle increases with decreasing PEG content in the copolymer, indicating that the hydrophilicity of the copolymer is proportional to the PEG content in the copolymer. The water contact angle on the surface of the samples is measured every five minutes. The contact angle of all samples decrease with the increase of time, including hydrophobic samples, which indicates that the porous structure of electrospun material had good water absorption, and the change rate of contact angle increases with the increase of PEG content.

The proportions of PEG block also have a great influence on the mechanical properties of the material. The mechanical properties of anastomosis stents prepared by PTMC-b-PEG-b-PTMC electrospinning are listed in Table 3. As the proportion of PEG block decreases, the tensile strength of the copolymer increases from 6.38 MPa to 12.75 MPa, respectively. This is because PEG is a semi-crystalline micro-phase state, which has plasticizing and hardening effects on the stent. With the increase of PEG, the crystallinity of the material increases and the tensile strength decreases.

Based on the comprehensive factors such as hydrophilicity and mechanical properties, in combination with the purpose, we believe that when the content of PEG is 10%~20%, its mechanical properties and hydrophilicity meet the requirements for implantation. In this range, the anastomosis stent has certain hydrophilicity, and has stable mechanical properties in dry and wet state, maintains certain mechanical strength and also has excellent flexibility, which ensures that it meets the strength without foreign body sensation and discomfort, and can be used as a good load-bearing repair tissue in intestinal trauma. Therefore, when PTMC-b-PEG-b-PTMC copolymer is used as the main base material, the rigid biodegradable polymer is added to make the anastomosis stent have better toughness, maintain a certain mechanical strength within two weeks after implantation, and the deformation of its cavity is minimal while the body type is degraded.

A sample with a PEG content of 15% is subsequently selected as the main base material of the anastomosis stent in the present disclosure, and is compounded with at least one of PLA, PCL and PBS and electrospun to prepare an intestinal anastomosis stent with a special structure and morphology.

TABLE 4

Different blending ratios of PTMC-b-PEG-b-PTMC copolymer and PLA, PCL, PBS and their mechanical properties after spinning

| Main substrate | Blends | Blending ratio | Thickness of anastomosis tube/mm | Tensile strength/ MPa | Elongation at break/ % |
|---|---|---|---|---|---|
| PTMC-b-PEG-b-PTMC copolymer | PLA | 5 | 0.22 | 10.32 | 237.6 |
| | | | 0.58 | 15.85 | 251.2 |
| | | 15 | 0.30 | 14.66 | 172.7 |
| | | | 0.55 | 18.21 | 202.5 |
| | | 30 | 0.20 | 15.55 | 87.3 |
| | | | 0.60 | 21.37 | 105.8 |
| | PCL | 5 | 0.31 | 12.63 | 285.4 |
| | | | 0.52 | 15.21 | 331.6 |
| | | 15 | 0.20 | 13.49 | 308.2 |
| | | | 0.46 | 16.88 | 352.8 |

TABLE 4-continued

Different blending ratios of PTMC-b-PEG-b-PTMC copolymer and
PLA, PCL, PBS and their mechanical properties after spinning

| Main substrate | Blends | Blending ratio | Thickness of anastomosis tube/mm | Tensile strength/ MPa | Elongation at break/ % |
|---|---|---|---|---|---|
| | | 30 | 0.28 | 15.62 | 343.7 |
| | | | 0.61 | 19.65 | 372.4 |
| | PBS | 5 | 0.32 | 11.57 | 265.4 |
| | | | 0.60 | 14.68 | 296.2 |
| | | 15 | 0.24 | 13.26 | 221.7 |
| | | | 0.57 | 16.63 | 262.6 |
| | | 30 | 0.35 | 16.49 | 161.8 |
| | | | 0.59 | 19.87 | 190.2 |

Instructions for each technician: although the present disclosure has been described with reference to the foregoing specific embodiments, the inventive concept is not limited to this disclosure, and any modifications using the inventive concept are intended to be included within the scope of the patent claims.

The foregoing description is only a preferred embodiment of the present disclosure, and the scope of the present disclosure is not limited to the above-mentioned embodiments, and all the technical solutions falling within the idea of the present disclosure fall within the scope of protection of the present disclosure. It should be noted that a person of ordinary skill in the art would have been able to make several improvements and modifications without departing from the principles of the present disclosure, and these improvements and modifications are also considered to be within the scope of the present disclosure.

The invention claimed is:

1. A novel flexible intestinal anastomosis stent, comprising a tubular stent body, which comprises a side wall, wherein an upper end and a lower end of the stent body are respectively an inlet end and an outlet end, the side wall of the stent body being provided with a plurality of special-shaped through holes, the through holes being horn-shaped, a large opening of the horn-shaped through holes being a liquid inlet hole on an outer side of the stent body, and a small opening thereof being a liquid outlet hole on an inner side of the stent body, the liquid inlet hole of each of the through holes being close to a side of the inlet end of the stent body, and the liquid outlet hole being close to a side of the outlet end of the stent body, the stent body being made of a flexible material, and the horn-shaped through holes on the side wall being pressed and deformed to discharge secretion in the through holes to an inside of the stent body via the liquid inlet holes, wherein a depth of the horn-shaped through hole is greater than that of the side wall of the intestinal anastomosis stent.

2. The novel flexible intestinal anastomosis stent according to claim 1, wherein an annular upper edge of the inlet end is provided with a boss, a lower edge of the outlet end having a concave polygonal structure, the concave polygonal structure forming a plurality of inwardly-folded wrinkle structures on the side wall of the stent body, each wrinkle structure of the plurality of wrinkle structures forming a reflex angle.

3. The novel flexible intestinal anastomosis stent according to claim 2, wherein the stent body comprises a suture site, the suture site comprising the annular upper edge of the inlet end and an inferior-angle edge of a lower edge of the concave polygonal structure of the outlet end.

4. The novel flexible intestinal anastomosis stent according to claim 2, wherein a length of each of the wrinkle structures is ½-⅔ of a height of the stent body.

5. The novel flexible intestinal anastomosis stent according to claim 4, wherein a thickness of the inner wall of the stent body is 0.20-0.6 mm.

6. The novel flexible intestinal anastomosis stent according to claim 5, wherein a thickness of the side wall, at the wrinkle structure, of the intestinal anastomosis stent is smaller than a thickness of the side wall above the wrinkle structure.

7. The novel flexible intestinal anastomosis stent according to claim 1, wherein a depth of the horn-shaped through hole is 1-2 mm.

8. The novel flexible intestinal anastomosis stent according to claim 1, wherein the stent body is made of a bio-flexible elastomer based on PTMC-b-PEG-b-PTMC copolymer blended with at least one of PLA, PCL and PBS, a content of PEG in the PTMC-b-PEG-b-PTMC copolymer is 10%-20%, and a blending ratio of the at least one of PLA, PCL and PBS is 5-30%.

9. A method of preparing the flexible intestinal anastomosis stent of claim 1, comprising the following steps:
(1) synthesis of PTMC-b-PEG-b-PTMC copolymer: adding a solution of 95-80 wt % of TMC monomer, 5-20 wt % of PEG5000 and 1-5 wt % of catalyst $Sn(Oct)_2$ into a reaction tube under an anhydrous and oxygen-free environment, placing a magneton in the reaction tube, sealing a tube opening after ensuring that the reaction tube is anhydrous and oxygen-free, sealing the tube opening to ensure that no oxygen and moisture enter, placing the reaction tube into an oil bath for a reaction, a temperature being 120-150° C., a reaction time being 24-48 h, and after the reaction is finished, taking out the solution for use;
(2) dissolution of PTMC-b-PEG-b-PTMC: according to a solid-liquid ratio of 1:5, using $CHCl_3$ or DMF or THF to dissolve the PTMC-b-PEG-b-PTMC copolymer, first washing the inner wall with $CHCl_3$ or DMF or THF for a plurality of times, washing away silicone grease and unreacted monomers, then adding an excess of $CHCl_3$ or DMF or THF, placing the solution on a shaker, a temperature of the shaker being set at 37° C., and waiting for the solution to completely dissolve;
(3) purification of PTMC-b-PEG-b-PTMC: the dissolved solution being slowly poured into a beaker containing n-hexane or ethanol for purification, slowly poured and continuously stirred, and the obtained flocculent PTMC-b-PEG-b-PTMC being suction-filtered, followed by vacuum drying for 48 h;
(4) preparation of electrospinning solution: compounding a PTMC-b-PEG-b-PTMC copolymer and at least one of PLA, PCL, PBS into a solvent DMF/THF, DMF:THF=1:1, a mass fraction of the solution being 5-10 wt %, and the solution being placed on a constant temperature shaker at 37° C. for 24 h until complete dissolution, and the electrospinning operation being performed after the dissolution is complete;
(5) preparation of anastomosis tube by electrospinning: performing electrospinning on an electrospinning apparatus to obtain the flexible intestinal anastomosis stent according to claim 1, electrospinning parameters being: a voltage of (−5, 30) V; a needle pushing speed of V=1.0-5.0 ml/h; a roller speed of V=100-500 RPM; a temperature of T=25-35° C.; a humidity of WET=20-40%.

* * * * *